United States Patent [19]
Graser

[11] Patent Number: 6,004,321
[45] Date of Patent: Dec. 21, 1999

[54] CANNULATED SCREW RETRACTION APPARATUS AND METHOD OF RETRACTION

[76] Inventor: Robert E. Graser, 7333 Barlite, Suite 330, San Antonio, Tex. 78224

[21] Appl. No.: 09/044,637

[22] Filed: Mar. 19, 1998

[51] Int. Cl.[6] .................................................. A61B 17/88
[52] U.S. Cl. .................................. 606/53; 606/80
[58] Field of Search ........................ 606/80, 79, 73, 606/72, 104

[56] References Cited

U.S. PATENT DOCUMENTS

| | | | |
|---|---|---|---|
| 4,978,350 | 12/1990 | Wagenknecht | 606/72 |
| 5,354,299 | 10/1994 | Coleman | 606/73 |
| 5,562,673 | 10/1996 | Koblish et al. | 606/80 |
| 5,573,537 | 11/1996 | Rogozinski | 606/80 |
| 5,697,935 | 12/1997 | Moran et al. | 606/104 |

*Primary Examiner*—Micheal Buiz
*Assistant Examiner*—David O. Reip
*Attorney, Agent, or Firm*—Jenkens & Gilchrist

[57] ABSTRACT

An apparatus and method for retrieval of fractured cannulated screws used for bone fixation. The retractor comprises a retraction shaft having a proximal end and a distal end, a tool shaft connected to the proximal end, a body having a reverse helix connected to the distal end, and a feeler shaft having a point connected to the body.

7 Claims, 1 Drawing Sheet

CANNULATED SCREW RETRACTION APPARATUS AND METHOD OF RETRACTION

BACKGROUND OF THE INVENTION

1. Technical Field

This invention relates generally a method and apparatus for the extraction of cannulated screws. More particularly, the instant invention relates to a method and apparatus for the extraction of a fractured, cannulated screw which has been fixated in bone.

2. History of Related Art

Many corrective surgical procedures involve the resection and subsequent fixation of bone. During the healing process, due to misdirected or excessive loading, the fixating screw, which is commonly cannulated, may be broken by a shearing action which occurs at the interface between the fixated surfaces.

The current state of technology encourages doctors in the surgical field to remove the fractured ends of the bone using a hollow boring drill and removing a large trephine of bone, with the broken internal fixation (i.e., screw) contained within the plug of bone so removed. This approach destroys a portion of the bone, and leaves a large defect within the patient that does not lend itself to easy refixation.

Some manufacturers have attempted to provide various retraction systems to grab the outside threads of a buried screw, usually on the surface of the bone, at the bone/screw interface, and then removing the screw by inducing a counter-clockwise rotation. However, this approach also tends to bore into the bone and several different sizes of retractors may be required to accomplish the task.

Further, if the fracture is not detected for some time, it is quite common for new bone growth to occur over and into the cavity formed by the cannula. This new growth must be removed to retrieve the fractured screw and such retrieval should be accomplished with a minimum of bone growth removal.

Therefore, what is needed is a retraction system for fractured, cannulated screws fixated in bone which does not require the removal of additional bone to retrieve the fractured internal fixation. Further, such a retraction system should allow for easy refixation, and accomplish the task with a minimum number of elements.

Finally, such a system should be easily accommodated by standard surgical power implements and operate to free the internal fixation from the bone even after new growth has entered into the cannulated area.

SUMMARY OF THE INVENTION

The present invention consists of a retractor for fractured cannulated screws fixated in bone, comprising a retraction shaft having a proximal end and a distal end; a tool shaft connected to the proximal end; a body having a reverse helix connected to the distal end; and a feeler shaft having a point connected to the body. The retractor may be made of stainless steel or carbide. The retraction shaft may be from about 1 to about 10 times the length of the tool shaft (most preferably about 5 times the length of the tool shaft) and from about 4 to about 12 times the length of the body (most preferably about 8 times the length of the body). The body of the retractor may be from about one-half to about 4 times the length of the feeler shaft, and is most preferably the same length as the feeler shaft. The reverse helix has a multiplicity of flutes. The retractor point may be a trocar point, a chisel point, or a multi-facet point.

The present invention also provides a method of retrieving a fractured cannulated screw fixated in a bone, comprising the steps of incising flesh to expose an open end of the screw; seating a retractor having a point into the open end of the screw; affixing a tool to the retractor; and turning the retractor using the tool so as to retrieve the screw from the bone. The present method of retrieving a fractured cannulated screw fixated in a bone may also comprise the step of driving the point into an open end of a screw to remove occluding bone growth therein. The seating step may further comprise tapping the retractor into the open end of the screw. The turning step may further comprise applying manual pressure downward onto a power tool and moving the retractor in a counter-clockwise direction.

The present invention also provides a method of retrieving a fractured cannulated screw fixated in a bone, comprising the steps of incising flesh to expose an open end of the screw; seating a retractor into the open end, the retractor comprising a retraction shaft having a proximal end and a distal end, a tool shaft connected to the proximal end, a body connected to the distal end, the body having a reverse helix, and a feeler shaft connected to the body, the feeler shaft having a point; affixing a tool to the retractor; and turning the retractor using the tool so as to retrieve the screw from the bone. The method of retrieving a fractured cannulated screw fixated in a bone may further comprise the step of driving the point into the open end of the screw to remove occluding bone growth therein.

BRIEF DESCRIPTION OF TE DRAWINGS

A more complete understanding of the structure and operation of the present invention may be had by reference to the following detailed description when taken in conjunction with the accompanying drawings, wherein.

Figure 6A:

FIGS. 6A a nd 6B illustrate side and top views, respectively, of the retractor point, wherein said point is a four-facet point.

DETAILED DESCRIPTION OF PRESENTLY PREFERRED EXEMPLARY EMBODIMENTS

In the preferred embodiment of the present invention, a retractor 10 includes a retraction shaft 20, having a proximal end 30 and distal end 40. A tool shaft 50 is connected to the distal end 40, being formed for reception by a Jacobs tool chuck. The proximal end 30 is connected to a body 60, having a reverse helix 90. A feeler shaft 70 is in turn connected to the body 60, and the feeler shaft 70 has a point 80.

The instant invention is designed specifically for the retraction of cannulated screws which have been used to fixate bone surfaces, and which, due to excessive loading or accidents, have been broken (i.e., sheared) at the fixation interface. However, the apparatus described herein can also be used for the removal of screws or other objects having a conventional threaded outer surface and a centralized entry passage, or cannula, present therein.

The feeler shaft 70 serves to guide the body 60 for seating at the entry to the fractured cannula. In addition, the point 80 serves to bore through any bone which may have grown within the cannula during the time between fracture of the screw and reentry by the surgeon into the affected area for removal of the fractured screw and refixation. While the retractor 10 can be made of carbide, ceramic, diamond, or a combination of these materials, fabrication costs, and the fact that most surgical implants are made of 3/16 or 3/16L grade stainless steel, dictate a preference for fabricating the retractor 10 from 17/4 stainless steel, heat treated at 900° F. to produce a Rockwell hardness of 40.

Figure 1:
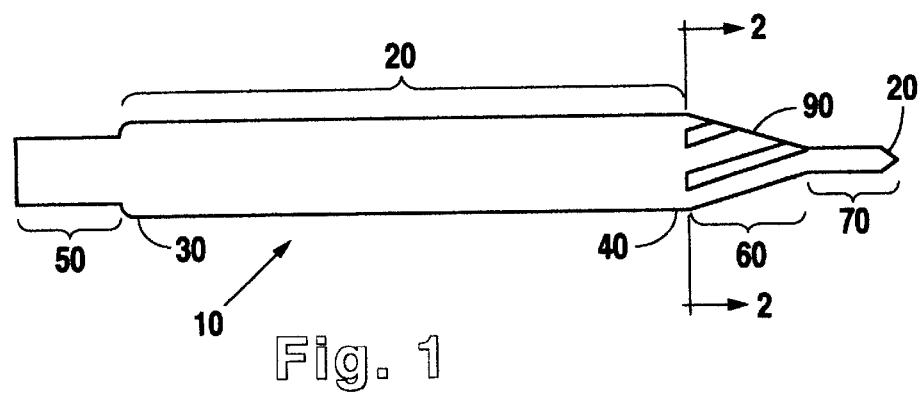
FIG. 1 is a side view of a retractor embodying the present invention.
Figure 2:
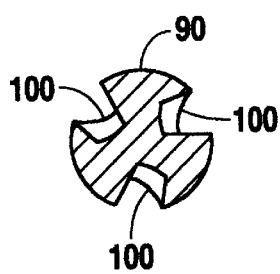
FIG. 2 is a sectioned view of the retractor embodying the present invention, taken at the interface between the retraction shaft and the body.

Once the point 80 of the retractor 10 has been manually placed at the entry of the fractured cannula, the retractor 10 can then be properly seated into the fractured screw by tapping the tool shaft 50 with a mallet or other impacting device until the point 80 has begun entry into the fractured cannula. At this time, a K-wire power tool, or other device capable of imparting rotation to the retractor 10, can be affixed to the tool shaft 50. With manual pressure downward, and counter-clockwise rotation of the power tool, the self-tapping, reverse helix 90 will begin to bite into the softer material of the screw and pull the screw back along its initial entry path for easy retrieval. As shown in FIG. 2, the flutes 100 should be of sufficient depth to allow use of the retractor 10 with several sizes of cannulated fixation screws.

Figure 3A:
FIGS. 3A and 3B illustrate side and top views, respectively, of the retractor point, wherein said point is a trocar point.
Figure 3B:
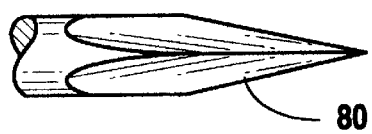
Figure 4A:
FIGS. 4A and 4B illustrate side and top views, respectively, of the retractor point, wherein said point is a chisel point.
Figure 5A:
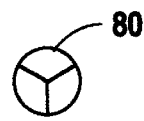
FIGS. 5A and 5B illustrate side and top views, respectively, of the retractor point, wherein said point is a three-facet point.
Figure 4B:
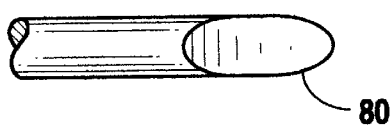
Figure 5B:
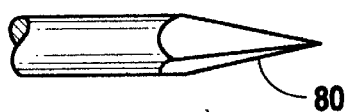
Figure 6B:

Several types of points 80 may be useful in the implementation and the instant invention. For example, a trocar point, as seen in FIGS. 3A and 3B, may be most useful for boring into bone which occludes entry to the fractured cannula. However, in other circumstances, a chisel point 80, as shown in FIGS. 4A and 4B, may be utilized. Multi-faceted points 80, such as are shown in FIGS. 5A and 5B (three-facet), and FIGS. 6A and 6B (four-facet), may also be used. A two-facet point 80 may also be useful, and although not illustrated, would have an appearance very similar to the tip of a common screwdriver.

While the retractor 10 may be fabricated in any number of sizes, some dimensions are more preferable than others when used in the particular case of retracting cannulated screws used in the fixation of bone. The inner diameter of cannulas for these screws normally ranges from about 1.1 mm to 2.8 mm. To accommodate the entire range of sizes, the length of the retraction shaft 20 is preferably from about 1.5 inches to about 2.0 inches The retraction shaft 20 is typically about one to about ten times the length of the tool shaft 50, which is most preferably about 3/8 in. long, so that the retraction shaft 20 is about five times the length of the tool shaft 20. Further, the length of the retraction shaft 20 is typically about four to about twelve times the length of the body, and is most preferably about eight times the length of the body 60, which is therefore about 0.25 in. long. The length of the body 60 is about one-half to about four times the length of the feeler shaft 70, and is most preferably about the same length as the feeler shaft 70. Therefore, the feeler shaft is most preferably also about 0.25 in. long.

While it is most preferable to have a larger number of flutes 100 on the body 60, for practical reasons, it is often not possible to have more than two flutes 100 existing on smaller sizes of the retractor 10. Therefore, while a multiplicity of flutes 100 exists along the reverse helix 90, the actual number may as few as two. The angle of the flutes 100 is typically from about 0° to about 45°, with the most preferable angle being about 5°.

For the larger sizes of cannulated screws used in bone fixation, the diameter of the feeler shaft 70 is most preferably about 0.062 in., and the diameter of the distal end 40 of the retraction shaft 20 is most preferably about 0.115 in. Also, for the larger sizes of cannulated screws, it is most preferable to taper the retraction shaft diameter from about 0.115 in. at the distal end 40 to a diameter of about 0.100 in. at the proximal end 30. This back-taper helps prevent binding within the bone and other material surrounding the retractor 10 during the retraction process. For the smaller sizes of cannulated screw, the most preferable size of the feeler shaft 70 is about 0.035 in. in diameter. The distal end 40 of the retraction shaft 20 is most preferably about 0.070 in. in diameter, and does not taper by any appreciable amount toward the proximal end 30. This is because the standard size Jacobs chuck power tool easily accepts a tool shaft 50 diameter of 0.062 in. This tool shaft 50 diameter is used on both the larger and smaller sizes of retractors 10, but may be fitted with flats on the sides for better gripping by the chuck. For additional strength, the steel shaft 50 can be made the same diameter as the retraction shaft. Since most surgical implants are made of 3/16 or 3/16L grade stainless steel, it is preferable to fabricate the retractor 10 from 17/4 stainless steel heat treated at 900° F. to produce a Rockwell hardness of 40.

The benefit of the retraction system embodied by the instant invention is that, by using an approach to the inside of the cannula, the retractor 10 may be implanted in the fractured screw without destroying the bone being fixated, and allows maintaining the existing thread contours. This approach allows a second screw, if needed, to be easily placed within the same hole without difficulty or damage from refixation.

Although the present invention is described in terms of a preferred exemplary embodiment with specific reference to use with cannulated screws for bone fixation, and a method of retrieving such screws after fracture, it is also applicable to other areas of art wherein a cannulated or other body having an internal orifice amenable to entry by the instant invention, and subsequent retrieval due to a threaded exterior, is possible. Such use is intended to fall within the scope of the following claims. Other aspects, features, and advantages of the present invention may be obtained from a study of this disclosure and the drawings, along with the appended claims.

What I claim is:

1. A method of retrieving a fractured cannulated screw fixated in a bone, comprising:

incising flesh to expose an open end of said screw;

seating a retractor having a self-tapping reverse helix and a point into said open end;

affixing a tool to said retractor;

turning said retractor using said tool so as to retrieve said screw from said bone.

2. The method of claim 1, further comprising the step of driving said point into said open end of said screw to remove occluding bone growth therein.

3. The method of claim 1, wherein said seating step further comprises tapping said retractor into said open end of said screw.

4. The method of claim 1, wherein said turning step further comprises applying manual pressure downward onto said power tool.

5. The method of claim 1, wherein said turning step further comprises moving said retractor in a counter-clockwise direction.

6. A method of retrieving a fractured cannulated screw fixated in a bone, comprising:

incising flesh to expose an open end of said screw;

seating a retractor into said open end, said retractor comprising a retraction shaft having a proximal end and a distal end, a tool shaft connected to said proximal end, a body connected to said distal end, said body having a reverse helix, and a feeler shaft connected to said body, said feeler shaft having a point;

affixing a tool to said retractor; and turning said retractor using said tool so as to retrieve said screw from said bone.

7. The method of claim 6, further comprising the step of driving said point into said open end of said screw to remove occluding bone growth therein.

* * * * *